(12) United States Patent
Westlund et al.

(10) Patent No.: US 6,706,018 B2
(45) Date of Patent: Mar. 16, 2004

(54) ADJUSTABLE LENGTH CATHETER ASSEMBLY

(75) Inventors: Randy Westlund, Minneapolis, MN (US); Bruce Tockman, Scandia, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 149 days.

(21) Appl. No.: 10/004,709

(22) Filed: Dec. 4, 2001

(65) Prior Publication Data

US 2003/0105451 A1 Jun. 5, 2003

(51) Int. Cl.7 ............................................. A61M 39/10
(52) U.S. Cl. ...................................... 604/194; 604/159
(58) Field of Search ................................. 604/159, 160, 604/198, 264, 165.01, 165.02

(56) References Cited

U.S. PATENT DOCUMENTS 5,334,187 A * 8/1994 Fischell et al. .............. 604/194
6,416,511 B1 * 7/2002 Lesh et al. .................... 606/41
2003/0120295 A1 * 6/2003 Simpson et al. ............ 606/159

* cited by examiner

Primary Examiner—Roy D. Gibson
Assistant Examiner—Aaron Roane
(74) Attorney, Agent, or Firm—Crawford Maunu PLLC

(57) ABSTRACT

A catheter assembly for cannulating a heart vessel includes a guide handle having proximal and distal ends, a lumen open at least at the distal end of the guide handle, and a stop member disposed within the lumen at a distal end of the guide handle. A catheter of the assembly has a proximal end disposed within the lumen of the guide handle and a preformed distal end. The catheter is longitudinally displaceable within the guide handle to adjust an exposed length of the distal end of the catheter. The stop member is engagable with the proximal end of the catheter to prevent the proximal end of the catheter from passing out of the guide handle. A locking mechanism within the guide handle to selectably prevents and permit axial rotation between the guide handle and catheter while permitting longitudinal displacement of the catheter within the guide handle.

43 Claims, 5 Drawing Sheets

ADJUSTABLE LENGTH CATHETER ASSEMBLY

FIELD OF THE INVENTION

The invention relates generally to guiding catheters, and more particularly to adjustable length guiding catheters used to locate and cannulate the coronary sinus of a patient's heart.

BACKGROUND OF THE INVENTION

Guiding catheters are instruments that allow a physician to locate and cannulate vessels in a patient's heart for performing various medical procedures, including venography and implanting of cardiac pacing devices. Cannulating heart vessels requires navigating a small diameter, flexible guide through the convoluted vasculature into a heart chamber, and then into a destination heart vessel. Once the destination heart vessel is reached, the catheter acts as a pathway for insertion of payloads into the vessel.

A commonly accessed destination vessel for cardiac pacing lead insertion is the coronary sinus. A pre-shaped guiding catheter is typically used to locate the coronary sinus ostium from the right atrium. There are numerous potential percutaneous access vessels that can be used for right atrium access. Common pathways include the left cephalic vein and the left subclavian vein. Depending on the patient anatomy and the pathway chosen, a specialized guiding catheter may be required.

Guiding catheter systems are typically configured with a profile and length that is optimized for the intended method of access. The contours of pre-shaped guiding catheters are generally fixed, and this is typically achieved in production by constraining the distal end within a shaping fixture while warming them until they assume the intended shape (i.e., by "heat setting" their polymer shaft).

A fixed shape catheter is adequate in many cases where the pathway is not significantly convoluted and the pathway does not deviate significantly between patients. In situations where structural anomalies or significant variations exist, use of a fixed shape catheter may require that the clinician stock multiple size and shapes of catheters to account for potential variations. Fixed shape catheters may require a time consuming trial and error process of inserting and removing different shapes until the destination vessel is successfully accessed. Further, the need to stock various sizes and shapes of guide catheters adds complexity and expense to the support of such procedures.

There is a need for an improved catheter assembly for accessing heart vessels that can dynamically account for anatomical variations and be adaptable for different methods of access. The present invention fulfills these and other needs, and addresses other deficiencies of prior art implementations and techniques.

SUMMARY OF THE INVENTION

The present invention is directed to a catheter assembly for cannulating a vessel of a patient's heart. According to one embodiment of the invention, a catheter assembly includes a guide handle having a proximal end, a distal end, a lumen open at least at the distal end of the guide handle, and a stop member disposed within the lumen at a distal end of the guide handle. The catheter assembly further includes a catheter having a proximal end disposed within the lumen of the guide handle. The catheter includes a preformed distal end, and the catheter is longitudinally displaceable within the guide handle to adjust an exposed length of the distal end of the catheter. The stop member is engagable with the proximal end of the catheter to prevent the proximal end of the catheter from passing out of the guide handle. A locking mechanism is provided within the guide handle. The locking mechanism engages the guide handle with the catheter to selectably prevent and permit axial rotation between the guide handle and catheter while permitting longitudinal displacement of the catheter within the guide handle.

In one configuration, the locking mechanism includes a locking arrangement longitudinally disposed along at least a portion of the guide handle lumen. The catheter further includes a locking arrangement longitudinally disposed along at least a-portion of the proximal end of the catheter. The respective locking arrangements of the catheter and guide handle engage and disengage to respectively prevent and permit axial rotation between the catheter relative to the guide handle while permitting longitudinal displacement of the catheter within the guide handle.

The locking mechanism can be engagable during extension and retraction of the catheter within the guide handle. Alternatively, the locking mechanism can be engagable only during full extension and full retraction of the catheter within the guide handle.

In one configuration, the locking mechanism includes a locking arrangement of the guide handle and a locking arrangement of the catheter. The locking arrangement of the guide handle includes at least one longitudinal groove at each of the proximal and distal ends of the guide handle. The locking arrangement of the catheter includes at least one longitudinal key at the proximal end of the catheter. The locking arrangement of the guide handle and the locking arrangement of the catheter can be engagable only at respective limits of longitudinal extension and longitudinal retraction of the catheter within the guide handle.

In another arrangement, a length of at least a portion of the guide handle lumen defines a travel length. The locking mechanism includes at least one longitudinal groove provided along a wall of the lumen. The catheter includes a locking member, including at least one longitudinal key having a length at least as long as the travel length of the lumen.

In one configuration of a catheter assembly according to the present invention, the exposed length of the distal end of the catheter can be adjustable within a range of 0 centimeters and about 15 centimeters. A length of the catheter assembly can range between about 40 centimeters and about 60 centimeters.

A catheter assembly according to the present invention can further include at least one electrode located at the distal end of the catheter. At least one electrical conductor can be disposed within the catheter and coupled to the electrode(s).

Other configurations include an occlusion device connected to the distal end of the catheter. Also, a hemostasis mechanism can be connected to the proximal end of the guide handle.

In one configuration, a seal can be included between the lumen of the guide handle and the catheter. The seal can include a plurality of O-rings or a leaflet seal between the lumen of the guide handle and the catheter. The seal can include a gel material or a hydrogel material provided between the lumen of the guide handle and the catheter.

In one configuration, the catheter has a diameterranging between about 8 French and about 10 French.

In another embodiment according to the present invention, a catheter assembly includes a guide handle having a distal end, a proximal end, a lumen open at the distal end of the guide handle, and a stop member disposed within the lumen at the distal end of the guide handle. A length of at least a portion of the lumen defines a travel length. The catheter assembly includes a catheter having a proximal end disposed within the lumen of the guide handle. The catheter further includes a preformed distal end. The catheter is longitudinally displaceable within the guide handle to adjust an exposed length of the distal end of the catheter by a maximum length corresponding to the travel length of the lumen. The stop member engages with the proximal end of the catheter to prevent the proximal end of the catheter from passing out of the guide handle.

In one configuration, the guide handle further includes a locking arrangement longitudinally disposed along at least a portion of the lumen. The catheter further comprises a locking arrangement longitudinally disposed along at least a portion of the proximal end of the catheter. The respective locking arrangements of the catheter and guide handle engage and disengage to respectively prevent and permit axial rotation between the catheter relative to the guide handle while permitting longitudinal displacement of the catheter within the guide handle. In one aspect, the respective locking arrangements of the guide handle and catheter are engagable during extension and retraction of the catheter within the guide handle. In another aspect, the respective locking arrangements of the guide handle and catheter are engagable only during full extension and full retraction of the catheter within the guide handle.

A configuration includes the locking arrangement of the guide handle having at least one longitudinal groove at each of the proximal and distal ends of the guide handle. The locking arrangement of the catheter has at least one longitudinal key at the proximal end of the catheter.

In another embodiment of the present invention, a method of inserting a payload into a coronary sinus of a patient's heart involves providing a guide catheter. The guide handle includes a proximal end, a distal end, a lumen open at least at the distal end of the guide handle, and a stop member disposed within the lumen at a distal end of the guide handle. The guide catheter further includes a catheter having a proximal end disposed within the lumen of the guide handle. The catheter has a preformed distal end. The catheter is longitudinally displaceable within the guide handle to adjust an exposed length of the distal end of the catheter. The stop member of the guide handle is engagable with the proximal end of the catheter to prevent the proximal end of the catheter from passing out of the guide handle. A locking mechanism is provided within the guide handle. The locking mechanism engages the guide handle with the catheter to selectably prevent and permit axial rotation between the guide handle and catheter while permitting longitudinal displacement of the catheter within the guide handle.

The method further involves inserting the preformed distal end of the catheter through a venous pathway via an access vessel. Longitudinally displacing the catheter within the guide handle adjusts an exposed length of the distal end of the catheter and accounts for variability of the venous pathway. Locking the guide handle and axially rotating the guide handle directs the preformed distal end of the catheter for finding and cannulating the patient's coronary sinus.

In one aspect of the method, a payload is advanced through the catheter to seat the payload into the coronary sinus after finding and cannulating the patient's coronary sinus. The payload can include an implantable cardiac lead. In another aspect of the method, a contrast media is injected through the catheter for mapping blood vessels after finding and cannulating the patient's coronary sinus.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
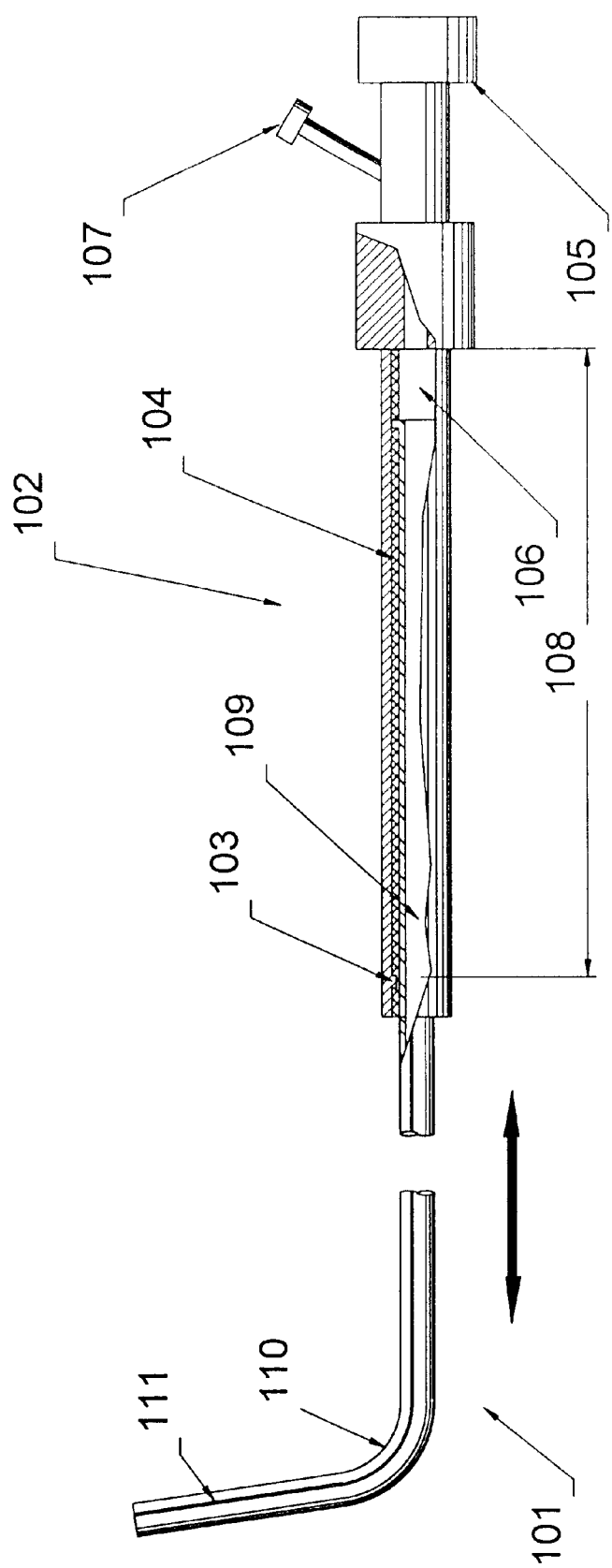
FIG. 1 is a cutaway view of a guide catheter embodying features of the present invention.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention. Referring now to the drawings, a catheter assembly according to the present invention is illustrated in FIG. 1. The catheter assembly includes a catheter 101 and a guide handle 102. A proximal section of the catheter 101 is movably disposed within an open lumen 106 of the guide handle 102 so that the catheter 101 is at least longitudinally displaceable within the guide handle 102. The guide handle 102 also includes a distally located stop member 103 that can prevent the catheter 101 from passing out of the guide handle 102. The guide handle 102 can also be configured such that the catheter 101 stops against a proximal end of the guide handle lumen 106. The distance that the catheter 101 can longitudinally move between the distal stop member 103 and the proximal end of the guide handle lumen 106 can define a travel length 108 of the catheter 101 within the guide handle lumen 106.

The travel length 108 influences the extent to which the catheter length can be adjusted. By allowing adjustable displacement of the catheter 101 within the guide handle 102, a catheter assembly according to the present invention provides an adjustable length guide useful for locating and cannulating vessels, particularly heart vessels. Such a catheter assembly can be used in place of multiple fixed length catheters for various medical procedures, including the implantation of cardiac pacing and defibrillation leads within the heart.

The guide handle 102 can be made of a relatively inflexible material, such as a rigid plastic or stainless steel. The guide handle 102 may include various attachments as shown in FIG. 1. These attachments include an injection port 107 and a hemostasis mechanism 105. The injection port 107 can provide the ability to inject medication or other fluids through the catheter lumen 106. In a particularaly useful application of a guide catheter according to the present invention, a radioopaque contrast media can be injected through the catheter lumen 106 for purposes of venography or angiography.

In another application of the catheter assembly, a payload, such as an implantable cardiac lead, is passed through the hemostasis mechanism 105 located at the proximal end of the guide handle. The hemostasis mechanism 105 (e.g. a hemostatic valve) prevents back bleeding and reduces the possibility of air embolism during introduction of payloads into the catheter assembly from the proximal end. In one configuration, the hemostasis mechanism 105 can be integrated into the guide handle 102. Alternatively, the hemostasis mechanism 105 can be a separate device that is attached after assembly of the guide handle 102. A separately attached hemostasis mechanism 105 can be connected using a standard luer fitting.

The catheter 101 is typically formed from an elongated, flexible tube sized appropriately for introduction and guidance through blood vessels, such as the vasculature leading to the heart. For cardiac access applications, the catheter diameter is typically about 8 French to about 10 French. In a configuration suited for cardiac implantation via the right atrium, the catheter ranges from about 55 to about 60 cm and is coupled with a guide handle 103 having travel length 108 of about 15 cm. The catheter 101 often includes an open lumen 109. The open lumen 109 has an inner diameter large enough to allow medical devices and payloads to pass through the lumen 109.

The catheter 101 can be made of a polymeric tube typically constructed of Pebax or other elastomeric compounds appropriate for medical uses. A tube made of Pebax will allow the catheter 101 to possess acceptable flexibility while being stiff enough to effectively transfer longitudinal pushing forces with good kink resistance. In applications requiring greater longitudinal stiffness or better kink resistance, a multi-layer tube construction is particularly useful. A multi-layer tube construction includes a braid or sheath within the tube walls. Such a braid or sheath can be made of stainless steel or a stiff artificial fiber. Methods of fabricating multi-layer tubes for medical applications are well known in the art.

An especially useful adaptation of the catheter 101 is to add a peel-away feature allowing the catheter 101 to be longitudinally split during retraction. A peel away feature typically includes a pre-stress line 111 disposed longitudinally along the length of the catheter 101. The pre-stress line 111 can be formed by creating a notch or groove in the catheter wall. Other methods of fabricating a pre-stress line 111 can include forming a longitudinal void or embedding a longitudinal fiber within the tube wall.

Another useful adaptation of the catheter 101 includes providing a lubricious liner within the open lumen 109. A lubricious liner can be formed of a fluoropolymer (e.g. PTFE) tubing. The lubricious liner helps reduce friction of payloads and other devices that are disposed within the catheter 101.

Referring still to FIG. 1, a curve 110 is pre-formed at the distal end of the catheter 101. The curve 110 can be thermoset on the catheter 101 during manufacture. The shape of the curve 110 can vary according to the intended application. For guiding the distal end of the catheter 101 through blood vessels, a substantially straight shape may suffice. For accessing the coronary sinus through a chamber of the heart, the curve 110 may be J- or U-shaped.

During the insertion and guiding phases of catheterization, the clinician may need to rotate the catheter 101 axially to maneuver the distal tip of the catheter 101 into a desired position. A catheter assembly according to the present invention beneficially provides a mechanism for locking relative rotation between the catheter 101 and the guide handle 102. The locking mechanism allows for the transmission of torque from the guide handle 102 to the catheter 101. This also enables the somewhat larger diameter guide handle 102 to act as a rotatable grip for the catheter 101.

Figure 2:
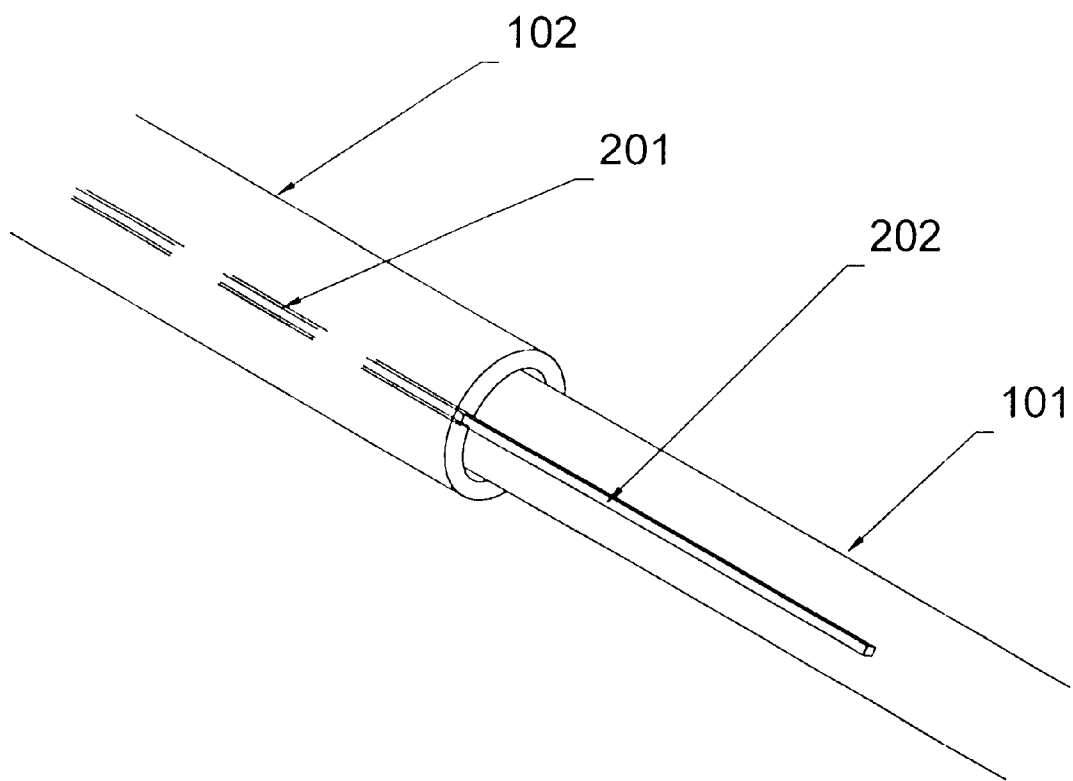
FIG. 2 is a view of the distal end of a guide handle showing details of a continuous locking mechanism according to an embodiment of the present invention.

Referring now to FIG. 2, one configuration of a locking mechanism is shown. The locking mechanism includes a locking groove 201 provided within the guide handle 102 and a key 202 fixably attached to the proximal end of the catheter 101. The key 202 can be an extruded feature on the catheter 101. Alternatively, the key 202 can be a separate piece of material that is bonded to the surface of the catheter 101.

In a particularly useful configuration, the locking groove 201 and key 202 are always engagable during the extension and retraction of the catheter 101 within the guide handle 102. One way of achieving engagability of the locking mechanism during catheter extension/retraction is to construct the key 202 to be at least as long as the catheter travel length 108. The travel length 108 of the catheter 101 is best illustrated in FIG. 1. The stop member 103 and the proximal end of the guide handle lumen 106 can also define the extension and retraction limits of the catheter 101. The catheter 101 can be defined as fully extended or retracted when a proximal end of the catheter 101 is prevented from further longitudinal movement by the stop member 103 and the proximal end of the lumen 106, respectively.

Figure 3A:
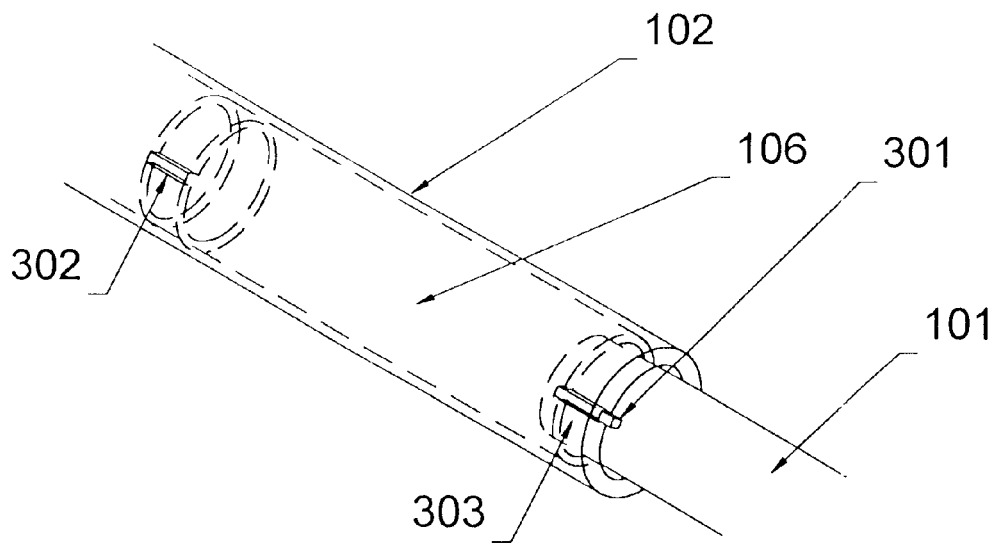
FIG. 3A is a view of the distal end of the guide handle showing details of a partial locking mechanism where a catheter is fully extended within the handle according to an embodiment of the present invention.
Figure 3B:
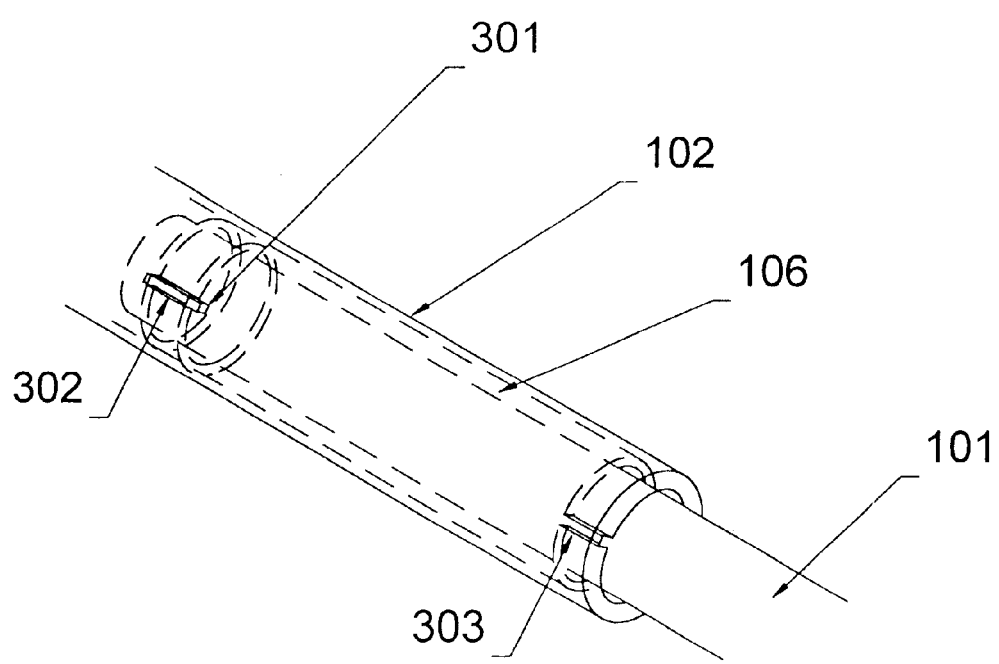
FIG. 3B is a view of the distal end of the guide handle of FIG. 3A where the catheter is fully retracted within the handle.

Another configuration of a locking mechanism is shown in FIGS. 3A and 3B. The mechanism in FIG. 3A includes a locking key 301 connected to catheter 101 and two locking grooves 301 and 302 in the guide handle 102. Locking grooves 301 and 302 are mounted near the proximal and distal ends, respectively, of the guide handle lumen 106. In FIG. 3A, the key 301 is engaging the groove 303 at or near full extension of the catheter 101. In FIG. 3B, the key 301 is engaging the groove 302 at or near full retraction of the catheter 101. At an extension position between full extension and full retraction of the inner catheter 101, the key 301 does not engage either of the grooves 302, 303, and the inner catheter 101 can be rotated relative to the guide handle 102. This allows catheter rotation to be selectively locked and unlocked by longitudinally extending the catheter 101 to an appropriate position relative to the guide handle 102.

Although only two locking grooves 302, 303 are shown in FIGS. 3A and 3B, it is understood that any number of locking grooves can be deployed within the guide handle 102 to allow a customized locking behavior appropriate for the intended catheter assembly application. This deployment of additional locking grooves can include multiple longitudinal locations of locking grooves, e.g. allowing locking at a midpoint between full extension and full retraction. Another aspect of utilizing additional locking grooves/keys can include deploying a plurality of locking grooves around a periphery of the guide handle 102 at one longitudinal location. This can serve to allow the catheter 101 to be locked at multiple predetermined axial rotation angles relative to the guide handle 102.

It is understood that other structural members known in the art can serve as locking members, and the description of a key and groove locking mechanism is only intended to illustrate one possible embodiment of such a mechanism. Other locking members known in the art, such as clamps, set screws and noncircular cross sectional profiles, can provide selectable rotational locking between the catheter 101 and guide handle 102.

Figure 4A:
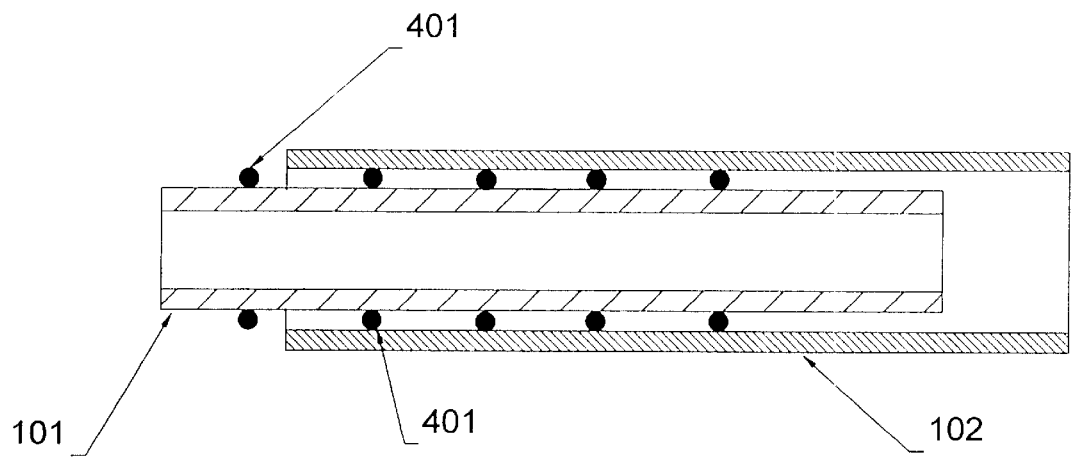
FIG. 4A is a longitudinal cross sectional of the guide handle and catheter using O-ring seals according to an embodiment of the present invention.

In another aspect of the present invention, a seal 104 is included between the guide handle 102 and the catheter 101. The seal 104 acts to prevent leakage of fluid and blood under venous or arterial pressure. Various configurations of the seal 104 are possible, one such configuration is illustrated in FIG. 4A. In FIG. 4A, a plurality of O-rings 401 are disposed between the catheter 101 and the guide handle 102. In the configuration illustrated, the O-rings 401 are situated between a smooth outer surface of the catheter 101 and a smooth inner surface of the guide handle 102. In another configuration, the O-rings 401 may also be fixably mounted in peripheral grooves on one or both of the guide handle 102 and catheter 101.

Figure 4B:
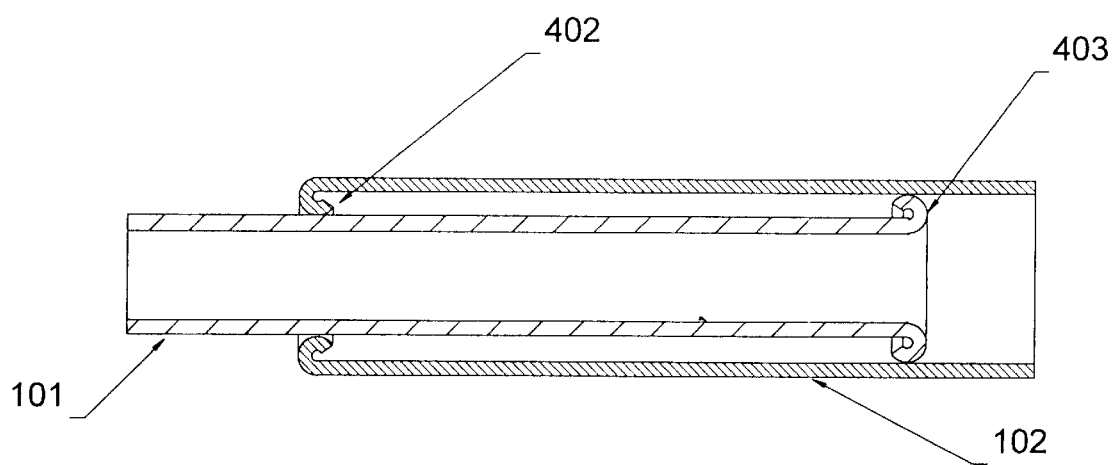
FIG. 4B is a longitudinal cross sectional of the guide handle and catheter using leaflet seals according to another embodiment of the present invention.

Another configuration of a seal is shown in FIG. 4B. This configuration includes leaflet seals 402, 403 on the guide handle 102 and catheter 101, respectively. The leaflet seals 402 and 403 can be formed on the guide handle 102 and catheter 101 by methods appropriate to the materials from which the guide handle 102 and catheter 101 are constructed. For example, if a metallic or plastic guide handle 102 is used, the rolled lip of the seal can be molded or machined. If the catheter 101 is formed of a flexible polymer tube, the seal 403 can be molded or thermoset in the polymer tube. Alternatively, a seal 402, 403 can be separately formed and then bonded to the catheter 101 and/or guide handle 102 during manufacture.

An alternate seal configuration includes disposing a hydrogel material between the catheter 101 and guide handle lumen 106. Such an arrangement is best seen in FIG. 1, where the seal 104 includes a coating of hydrogel material applied between to the catheter 101 and the guide handle 102. The seal 104 is preferably applied along a sufficient length of the guide handle lumen 106 to seal the proximal end of the catheter 101 over the full travel length 108.

Figure 5:
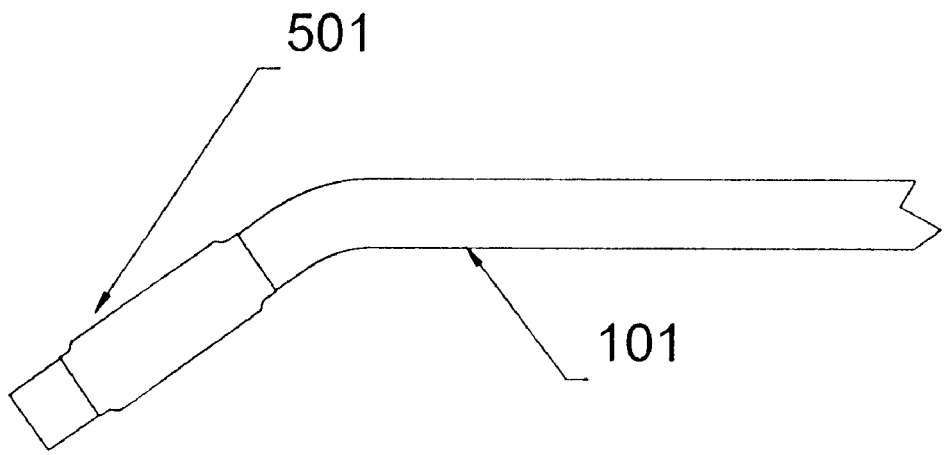
FIG. 5 is a view of a distal end of the catheter showing an attached occlusion balloon according to one embodiment of the present invention.

As shown in FIG. 5, another useful adaptation of a catheter assembly according to the present invention includes the addition of an occlusion balloon 501 to the distal end of the catheter 101. The catheter 101 in such an adaptation may also include a second lumen allowing inflation of the occlusion balloon 501 from a proximal end of the catheter 101.

The occlusion balloon 501 is typically constructed of soft, compliant latex material mounted on the distal end of the catheter 101. Occlusion balloons are best flush mounted, i.e. the occlusion balloon 501 is attached in such a way that the diameter of the deflated balloon 501 closely approximates the diameter of the catheter 101. In some configurations, the catheter 101 tapers near the distal tip, producing a low distal profile to facilitate atraumatic insertion, positioning and withdrawal of the catheter 101.

Figure 6:
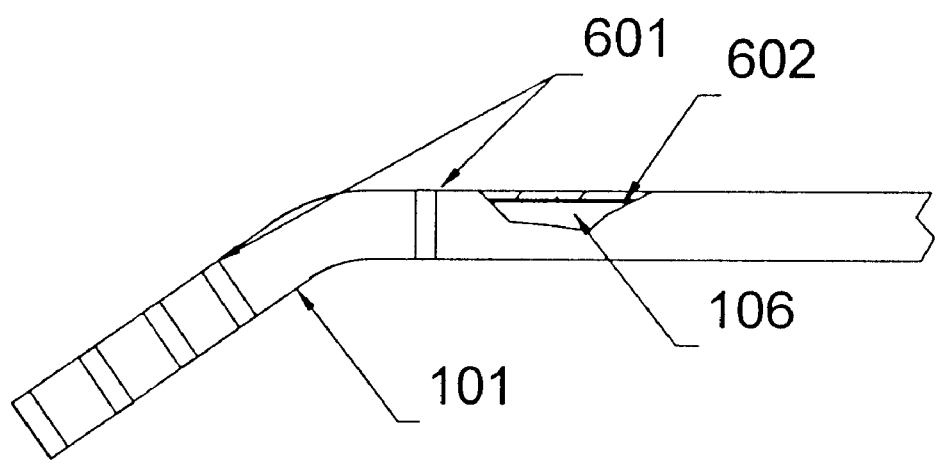
FIG. 6 is a view of a distal end of the catheter showing attached electrodes according to one embodiment of the present invention.

Another adaptation of a catheter assembly according to the present invention includes the addition of one or more electrodes to the catheter 101. This is best seen in FIG. 6. Electrodes 601 are preferably flush mounted at a distal end of the catheter 101. The electrodes 601 can be constructed of various materials depending on the intended application. For electrophysiology applications, electrodes 601 are typically constructed from stainless steel, silver or platinum. For ablation purposes, electrodes are typically constructed of platinum/iridium. At least one conductor 602 is coupled to the electrodes 601. The conductors 602 are disposed within the catheter 101 from the distal to proximal ends of the catheter 101. The conductors 602 can be disposed within the lumen 109 of the catheter 101. In another configuration, the conductors 602 can be embedded within the catheter walls.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A catheter assembly, comprising:
   a guide handle comprising a proximal end, a distal end, a lumen open at least at the distal end of the guide handle, and a stop member disposed within the lumen of the guide handle;
   a catheter comprising a proximal end disposed within the lumen of the guide handle and a preformed distal end, the catheter longitudinally displaceable within the guide handle to adjust an exposed length of the distal end of the catheter, the stop member engagable with the proximal end of the catheter to prevent the proximal end of the catheter from passing out of the guide handle; and
   a locking mechanism provided within the guide handle, the locking mechanism engaging the guide handle with the catheter to selectably prevent and permit axial rotation between the guide handle and catheter while permitting longitudinal displacement of the catheter within the guide handle.

2. A catheter assembly according to claim 1, wherein the locking mechanism comprises a locking arrangement longitudinally disposed along at least a portion of the lumen and the catheter further comprises a locking arrangement longitudinally disposed along at least a portion of the proximal end of the catheter, the respective locking arrangements of the catheter and guide handle engaging and disengaging to respectively prevent and permit axial rotation between the catheter relative to the guide handle while permitting longitudinal displacement of the catheter within the guide handle.

3. A catheter assembly according to claim 1, wherein the locking mechanism is engagable during extension and retraction of the catheter within the guide handle.

4. A catheter assembly according to claim 1, wherein the locking mechanism is engagable only during full extension and full retraction of the catheter within the guide handle.

5. A catheter assembly according to claim 1, wherein the locking mechanism comprises a locking arrangement of the guide handle and a locking arrangement of the catheter, the looking arrangement of the guide handle comprising at least one longitudinal groove at each of the proximal and distal ends of the guide handle, and the locking arrangement of the catheter comprising at least one longitudinal key at the proximal end of the catheter.

6. A catheter assembly according to claim 5, wherein the locking arrangement of the guide handle and the locking arrangement of the catheter are engagable only at respective limits of longitudinal extension and longitudinal retraction of the catheter within the guide handle.

7. A catheter assembly according to claim 1, wherein:
a length of at least a portion of the lumen defines a travel length;
the locking mechanism comprises at least one longitudinal groove provided along a wall of the lumen; and
the catheter comprises a locking member including at least one longitudinal key having a length at least as long as the travel length of the lumen.

8. A catheter assembly according to claim 1, wherein the exposed length of the distal end of the catheter is adjustable within a range of 0 centimeters and about 16 centimeters.

9. A catheter assembly according to claim 1, wherein a length of the catheter assembly ranges between about 40 centimeters and about 60 centimeters.

10. A catheter assembly according to claim 1, further comprising:
at least one electrode located at the distal end of the catheter; and
at least one electrical conductor disposed within the catheter and coupled to the at least one electrode.

11. A catheter assembly according to claim 1, further comprising an occlusion device connected to the distal end of the catheter.

12. A catheter assembly according to claim 1, further comprising a hemostasis mechanism connected to the proximal end of the guide handle.

13. A catheter assembly according to claim 1, further comprising a seal between the lumen of the guide handle and the catheter.

14. A catheter assembly according to claim 13, wherein the seal comprises a plurality of O-rings or a leaflet seal provided between the lumen of the guide handle and the catheter.

15. A catheter assembly according to claim 13, wherein the seal comprises a gel material or a hydrogel material provided between the lumen of the guide handle and the catheter.

16. A catheter assembly according to claim 1, wherein the catheter has a diameter ranging between about 8 French and about 10 French.

17. A catheter assembly comprising:
a guide handle comprising a distal end, a proximal end, and a lumen op en at the distal end of the guide handle, a length of at least a portion of the lumen defining a travel length;
a catheter comprising a proximal end disposed within the lumen of the guide handle and a shaped distal end, the catheter longitudinally displaceable within the guide handle to adjust an exposed length of the distal end of the catheter by a maximum length corresponding to the travel length of the lumen; and
a torque transmission mechanism provided at the guide handle, the torque transmission mechanism configured to engage the catheter to selectably prevent and permit axial rotation between the guide handle and catheter while permitting longitudinal displacement of the catheter within the guide handle.

18. A catheter assembly according to claim 17, wherein the travel length of the lumen ranges between about 5 centimeters and about 15 centimeters.

19. A catheter assembly according to claim 17, wherein the exposed length of the catheter ranges between about 40 centimeters and about 60 centimeters.

20. A catheter assembly according to claim 17, further comprising:
at least one electrode located at the distal end of the catheter; and
at least one electrical conductor disposed within the catheter and coupled to the at least one electrode.

21. A catheter assembly according to claim 17, further comprising an occlusion device connected to the distal end of the catheter.

22. A catheter assembly according to claim 17, further comprising a hemostasis mechanism connected to the proximal end of the guide handle.

23. A catheter assembly according to claim 17, further comprising a seal between the lumen of the guide handle and the catheter.

24. A catheter assembly according to claim 23, wherein the seal comprises a plurality of O-rings or a leaflet seal provided between the lumen of the guide handle and the catheter.

25. A catheter assembly according to claim 23, wherein the seal comprises a gel material or a hydrogel material provided between the lumen of the guide handle and the catheter.

26. A catheter assembly according to claim 17, wherein the torque transmission mechanism further comprises a locking arrangement longitudinally disposed along at least a portion of the lumen and the catheter further comprises a locking arrangement longitudinally disposed along at least a portion of the proximal end of the catheter, the respective locking arrangements of the catheter and guide handle engaging and disengaging to respectively prevent and permit axial rotation between the catheter relative to the guide handle while permitting longitudinal displacement of the catheter within the guide handle.

27. A catheter assembly according to claim 26, wherein the respective locking arrangements of the guide handle and catheter are engagable during extension and retraction of the catheter within the guide handle.

28. A catheter assembly according to claim 26, wherein the respective locking arrangements of the guide handle and catheter are engagable only during full extension and full retraction of the catheter within the guide handle.

29. A catheter assembly according to claim 26, wherein the locking arrangement of the guide handle comprises at least one longitudinal groove at each of the proximal and distal ends of the guide handle, and the locking arrangement of the catheter comprising at least one longitudinal key at the proximal end of the catheter.

30. A catheter assembly according to claim 17, wherein the catheter has a diameter ranging between about 8 French and about 10 French.

31. A method of inserting a payload into a coronary sinus of a patient's heart, comprising:
providing a guide catheter comprising:
a guide handle comprising a proximal end, a distal end, a lumen open at least at the distal end of the guide handle, and a stop member disposed within the lumen of the guide handle;

a catheter comprising a proximal end disposed within the lumen of the guide handle and a preformed distal end, the catheter longitudinally displaceable within the guide handle to adjust an exposed length of the distal end of the catheter, the stop member engagable with the proximal end of the catheter to prevent the proximal end of the catheter from passing out of the guide handle; and a locking mechanism provided within the guide handle, the locking mechanism engaging the guide handle with the catheter to selectably prevent and permit axial rotation between the guide handle and catheter while permitting longitudinal displacement of the catheter within the guide handle;

inserting the preformed distal end of the catheter through a venous pathway via an access vessel;

longitudinally displacing the catheter within the guide handle to adjust an exposed length of the distal end of the catheter and account for variability of the venous pathway; and locking the guide handle and axially rotating the guide handle to direct the preformed distal end of the catheter for finding and cannulating the patient's coronary sinus.

32. A method according to claim 31, further comprising advancing a payload through the catheter to seat the payload into the coronary sinus after finding and cannulating the patient's coronary sinus.

33. A method according to claim 32, wherein the payload comprises an implantable cardiac lead.

34. A method according to claim 31, further comprising injecting a contrast media through the catheter for mapping blood vessels after finding and cannulating the patient's coronary sinus.

35. A catheter assembly comprising:

a guide handle comprising a distal end, a proximal end, a lumen open at the distal end of the guide handle, and a stop member disposed within the lumen of the guide handle, a length of at least a portion of the lumen defining a travel length;

a catheter comprising a proximal end disposed within the lumen of the guide handle and a preformed distal end, the catheter longitudinally displaceable within the guide handle to adjust an exposed length of the distal end of the catheter by a maximum length corresponding to the travel length of the lumen, and the stop member engaging with the proximal end of the catheter to prevent the proximal end of the catheter from passing out of the guide handle; and a seal provided between the lumen of the guide handle and the catheter, the seal comprising a plurality of O-rings, and a torque transmission mechanism provided at the guide handle, the torque transmission mechanism configured to engage the catheter to selectively prevent and permit axial rotation between the guide handle and the catheter while permitting longitudinal displacement of the catheter within the guide handle.

36. The catheter assembly of claim 35, wherein the seal is configured to prevent leakage of fluid and blood under venous or arterial pressure.

37. The catheter assembly of claim 35, wherein the guide handle lumen comprises peripheral grooves, and at least some of the O-rings are fixably mounted in the peripheral grooves.

38. The catheter assembly of claim 35, wherein the catheter comprises peripheral grooves, and at least some of the O-rings are fixably mounted in the peripheral grooves.

39. A catheter assembly comprising:

a guide handle comprising a distal end, a proximal end, a lumen open at the distal end of the guide handle, and a stop member disposed within the lumen of the guide handle, a length of at least a portion of the lumen defining a travel length;

a catheter comprising a proximal end disposed within the lumen of the guide handle and a preformed distal end, the catheter longitudinally displaceable within the guide handle to adjust an exposed length of the distal end of the catheter by a maximum length corresponding to the travel length of the lumen, and the stop member engaging with the proximal end of the catheter to prevent the proximal end of the catheter from passing out of the guide handle; and a seal provided between the lumen of the guide handle and the catheter, the seal comprising a leaflet seal, and a torque transmission mechanism provided at the guide handle, the torque transmission mechanism configured to engage the catheter to selectively prevent and permit axial rotation between the guide handle and the catheter while permitting longitudinal displacement of the catheter within the guide handle.

40. The catheter assembly of claim 39, wherein the seal is configured to prevent leakage of fluid and blood under venous or arterial pressure.

41. A catheter assembly comprising:

a guide handle comprising a distal end, a proximal end, a lumen open at the distal end of the guide handle, and a stop member disposed within the lumen of the guide handle, a length of at least a portion of the lumen defining a travel length;

a catheter comprising a proximal end disposed within the lumen of the guide handle and a preformed distal end, the catheter longitudinally displaceable within the guide handle to adjust en exposed length of the distal end of the catheter by a maximum length corresponding to the travel length of the lumen, and the stop member engaging with the proximal end of the catheter to prevent the proximal end of the catheter from passing out of the guide handle; and a seal provided between the lumen of the guide handle and the catheter, the seal comprising gel material provided between the lumen of the guide handle and the catheter, and a torque transmission mechanism provided at the guide handle, the torque transmission mechanism configured to engage the catheter to selectively prevent and permit axial rotation between the guide handle and the catheter while permitting longitudinal displacement of the catheter within the guide handle.

42. The catheter assembly of claim 41, wherein seal comprises a hydrogel material provided between the lumen of the guide handle and the catheter.

43. The catheter assembly of claim 41, wherein the seal is configured to prevent leakage of fluid and blood under venous or arterial pressure.

* * * * *

UNITED STATES PATENT AND TRADEMARK OFFICE
CERTIFICATE OF CORRECTION

PATENT NO. : 6,706,018 B2  
DATED : March 16, 2004  
INVENTOR(S) : Westlund et al.

It is certified that error appears in the above-identified patent and that said Letters Patent is hereby corrected as shown below:

<u>Column 9,</u>  
Line 24, "16 centimeters" should read -- 15 centimeters --.

<u>Column 12,</u>  
Line 19, start a new paragraph beginning with the words " a seal provided…"

Signed and Sealed this

Fifteenth Day of June, 2004

JON W. DUDAS  
*Acting Director of the United States Patent and Trademark Office*